US012566151B2

(12) United States Patent
Kato et al.

(10) Patent No.: US 12,566,151 B2
(45) Date of Patent: Mar. 3, 2026

(54) SEMICONDUCTOR DEVICE AND CELL POTENTIAL MEASURING DEVICE

(71) Applicant: SONY SEMICONDUCTOR SOLUTIONS CORPORATION, Kanagawa (JP)

(72) Inventors: Yuri Kato, Kanagawa (JP); Koji Ogawa, Kanagawa (JP)

(73) Assignee: SONY SEMICONDUCTOR SOLUTIONS CORPORATION, Kanagawa (JP)

( * ) Notice: Subject to any disclaimer, the term of this patent is extended or adjusted under 35 U.S.C. 154(b) by 592 days.

(21) Appl. No.: 17/999,860

(22) PCT Filed: May 27, 2021

(86) PCT No.: PCT/JP2021/020125
§ 371 (c)(1),
(2) Date: Nov. 24, 2022

(87) PCT Pub. No.: WO2021/251155
PCT Pub. Date: Dec. 16, 2021

(65) Prior Publication Data
US 2023/0213475 A1     Jul. 6, 2023

(30) Foreign Application Priority Data
Jun. 10, 2020     (JP) ................................ 2020-100623

(51) Int. Cl.
*G01N 27/414* (2006.01)
*C12M 1/34* (2006.01)
*H03F 3/45* (2006.01)

(52) U.S. Cl.
CPC ......... *G01N 27/4145* (2013.01); *C12M 41/46* (2013.01); *H03F 3/45269* (2013.01); *H03F 2203/45156* (2013.01)

(58) Field of Classification Search
CPC .............. C12M 41/46; G01N 15/1031; G01N 27/4145; G01N 2015/1006;
(Continued)

(56)     References Cited

U.S. PATENT DOCUMENTS

2016/0245788 A1 * 8/2016 Wang ................. G01N 33/4836
2020/0018742 A1    1/2020 Lopez

FOREIGN PATENT DOCUMENTS

EP      1278064 A1 * 1/2003 ......... G01N 33/4836
JP   05-210986 A    8/1993
(Continued)

OTHER PUBLICATIONS

Machine Translation of JP 2020051882A (Year: 2025).*
(Continued)

*Primary Examiner* — Michael L Hobbs
(74) *Attorney, Agent, or Firm* — CHIP LAW GROUP

(57)     ABSTRACT

The present disclosure relates to a semiconductor device and a cell potential measuring device capable of improving measurement accuracy of a potential of a solution. A semiconductor device includes a read electrode that reads a potential of a solution, a differential amplifier, a first capacitor connected in series in a loop feeding back an output of the differential amplifier to a second input different from a first input from the read electrode, a resistance element connected in parallel with the first capacitor, and a second capacitor connected between a reference electrode indicating a reference potential and the second input. The present disclosure can be applied to, for example, a cell potential measuring device.

17 Claims, 11 Drawing Sheets

(58) Field of Classification Search
CPC ............ H03F 3/45183; H03F 3/45269; H03F
3/45475; H03F 2203/45156; H03F
2203/45514
See application file for complete search history.

(56) References Cited

FOREIGN PATENT DOCUMENTS

| | | | | | |
|---|---|---|---|---|---|
| JP | 2020-051882 A | | 4/2020 | | |
| JP | 2020051882 | * | 4/2020 | ............. | C12M 3/00 |
| WO | 2005/080956 A1 | | 9/2005 | | |
| WO | WO-2017221714 A1 | * | 12/2017 | ......... | G01N 27/4148 |

OTHER PUBLICATIONS

International Search Report and Written Opinion of PCT Application No. PCT/JP2021/020125, issued on Aug. 3, 2021, 10 pages of ISRWO.
Harrison, et al., "A low-power low-noise CMOS amplifier for neural recording applications", IEEE Journal of Solid-State Circuits, vol. 38, No. 6, Jun. 5, 2003, pp. 958-965.

* cited by examiner

SEMICONDUCTOR DEVICE AND CELL POTENTIAL MEASURING DEVICE

CROSS REFERENCE TO RELATED APPLICATIONS

This application is a U.S. National Phase of International Patent Application No. PCT/JP2021/020125 filed on May 27, 2021, which claims priority benefit of Japanese Patent Application No. JP 2020-100623 filed in the Japan Patent Office on Jun. 10, 2020. Each of the above-referenced applications is hereby incorporated herein by reference in its entirety.

TECHNICAL FIELD

The present disclosure relates to a semiconductor device and a cell potential measuring device, and more particularly to a semiconductor device and a cell potential measuring device capable of improving measurement accuracy of a potential of a solution.

BACKGROUND ART

Conventionally, a cell potential measuring device including a single feedback auto-zero differential amplifier has been proposed (see, for example, Patent Document 1).

In the differential amplifier of Patent Document 1, a read electrode is connected to a diode-connected pMOS transistor side input transistor of a current mirror circuit serving as a load resistor, and an output of the differential amplifier is fed back to a non-diode-connected pMOS transistor side input transistor to form a closed loop. Furthermore, a reference electrode is connected to the input transistor on the non-diode-connected pMOS transistor side via a sampling capacitor. Then, a potential that is serving the operating point of the differential amplifier is sampled and held in the sampling capacitor by the reset operation. Furthermore, in order to prevent fluctuation of the potential of the sampling capacitor due to the leakage current, the reset operation is periodically performed.

CITATION LIST

Patent Document

Patent Document 1: International Patent Application No. 2017/221714

SUMMARY OF THE INVENTION

Problems to be Solved by the Invention

However, the cell potential measuring device of Patent Document 1 cannot detect a signal in a frequency band lower than the cutoff frequency based on the period of the reset operation of the sampling capacitor, so that the measurement accuracy of the potential of the solution may be deteriorated.

The present disclosure has been made in view of such a situation, and is directed to improve the measurement accuracy of the potential of the solution.

Solutions to Problems

A semiconductor device according to a first aspect of the present disclosure includes a read electrode that reads a potential of a solution, a differential amplifier, a first capacitor connected in series in a loop feeding back an output of the differential amplifier to a second input different from a first input from the read electrode, a resistance element connected in parallel with the first capacitor, and a second capacitor connected between a reference electrode indicating a reference potential and the second input.

A cell potential measuring device according to a second aspect of the present disclosure includes a read electrode that reads a potential of a cell contained in a solution, a differential amplifier, a first capacitor connected in series in a loop feeding back an output of the differential amplifier to a second input different from a first input from the read electrode, a resistance element connected in parallel with the first capacitor, and a second capacitor connected between a reference electrode indicating a reference potential and the second input.

In the first aspect of the present disclosure, the potential of the solution is read, and a signal indicating the read potential is output.

According to a second aspect of the present disclosure, a potential of a cell contained in a solution is read, and a signal indicating the read potential is output.

BRIEF DESCRIPTION OF DRAWINGS

FIG. 1 is a circuit diagram illustrating a configuration of a sensor of Patent Document 1.

FIG. 4 is a circuit diagram illustrating a configuration example of a first embodiment of a cell potential measuring device to which the present disclosure is applied.

FIG. 6 is a circuit diagram illustrating a detailed configuration example of the sensor in FIG. 5.

FIG. 8 is a circuit diagram illustrating a configuration example of a second embodiment of a sensor to which the present disclosure is applied.

FIG. 9 is a circuit diagram illustrating a configuration example of a third embodiment of a sensor to which the present disclosure is applied.

MODE FOR CARRYING OUT THE INVENTION

Hereinafter, aspects for carrying out the present disclosure (hereinafter, referred to as embodiments) will be described. Note that the description will be given in the following order.

Figure 10:
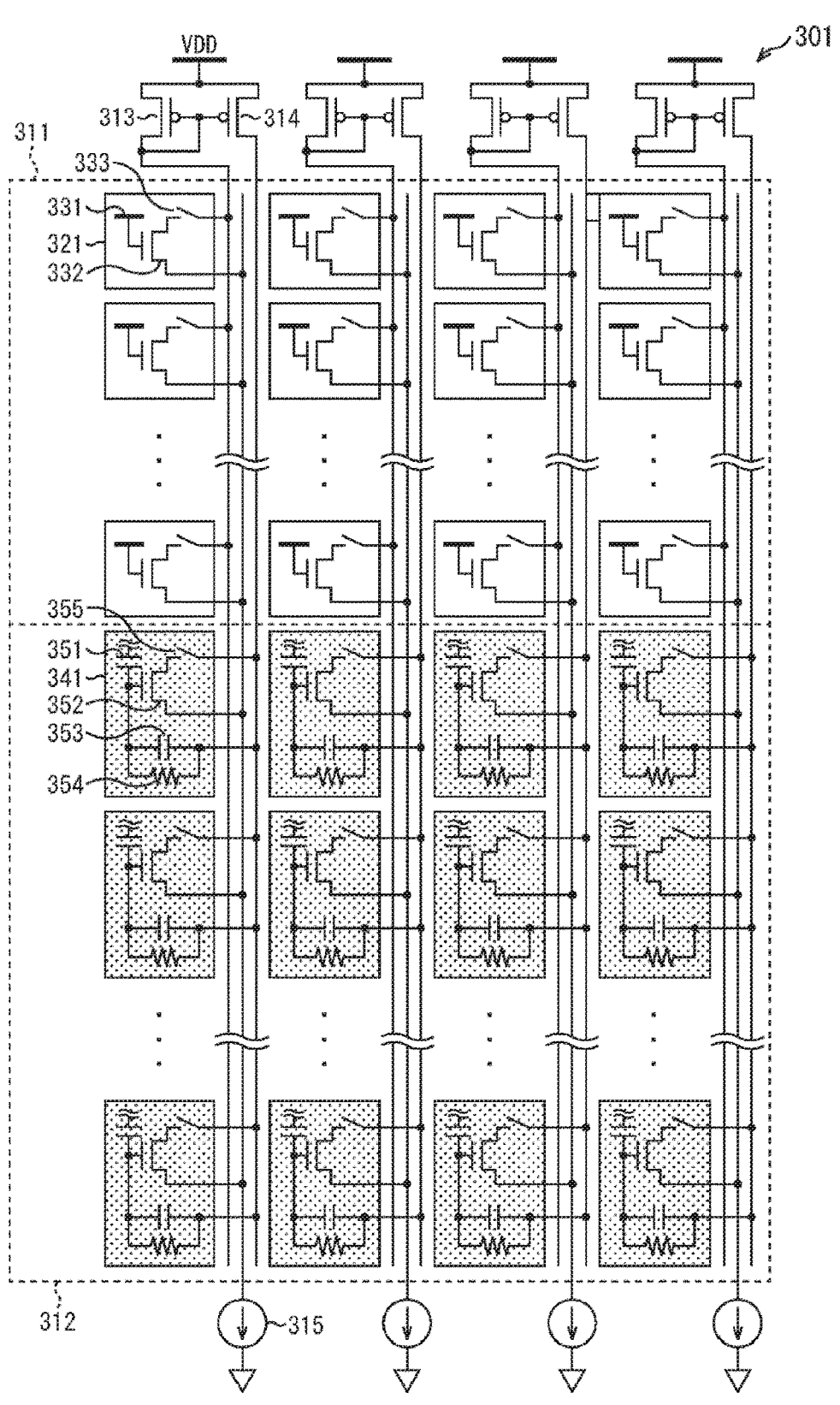
FIG. 10 is a circuit diagram illustrating a configuration example of a second embodiment of a sensing unit to which the present disclosure is applied.

1. Background of the Present Disclosure (FIGS. 1 to 3)
2. First Embodiment: Cell Potential Measuring Device (FIGS. 4 to 7)
3. Second embodiment: Sensor (FIG. 8)
4. Third embodiment: Sensor (FIG. 9)
5. Fourth Embodiment: Sensing Unit (FIG. 10)

6. Fifth Embodiment: Cell Potential Measuring Device
   (FIG. 11)
7. Modifications
8. Others

1. Background of the Present Disclosure

Background of the present disclosure will be described with reference to FIGS. 1 to 3.

Figure 1:
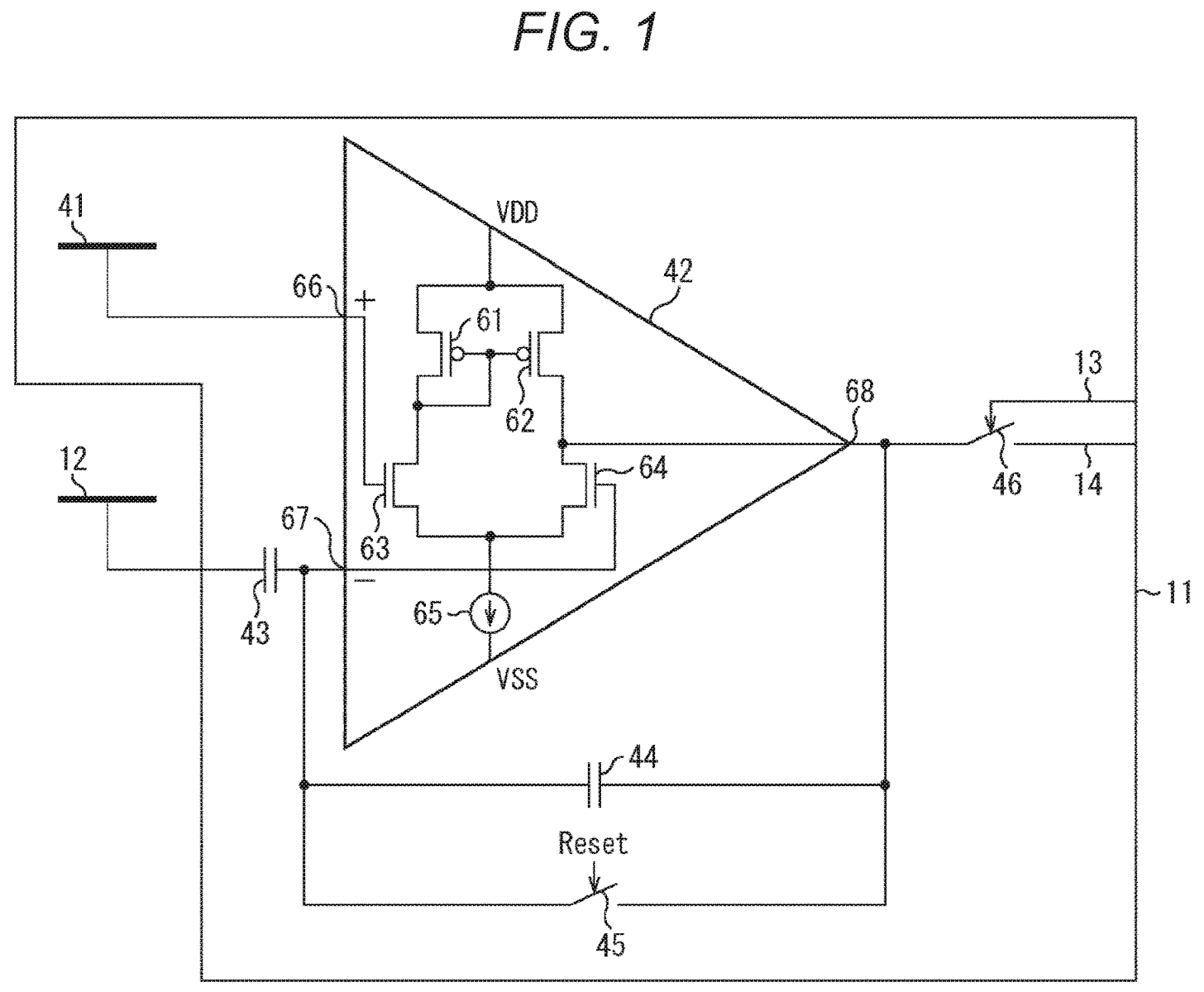

FIG. 1 is a circuit diagram illustrating a configuration of a sensor 11 constituting the cell potential measuring device of Patent Document 1 described above.

The sensor 11 includes a read electrode 41, a differential amplifier 42, a capacitor 43, a capacitor 44, a reset switch 45, and a switch 46. The differential amplifier 42 includes a load transistor 61 and a load transistor 62 each including a pMOS transistor, an input transistor 63 and an input transistor 64 each including an nMOS transistor, a constant current source 65, an input terminal 66, an input terminal 67, and an output terminal 68.

The read electrode 41 is disposed in a culture solution that is a solution containing biological cells to read the potential of the culture solution as the potential of the biological cells. The read electrode 41 is connected to the input terminal 66 of the differential amplifier 42 to input an electric signal indicating the read potential (hereinafter, referred to as a cell potential signal) to the input terminal 66.

A reference electrode 12 is disposed at a position away from the biological cells in the culture solution to read a reference potential of the culture solution. The reference electrode 12 is connected to the input terminal 67 of the differential amplifier 42 via the capacitor 43 to input an electric signal indicating the read reference potential (hereinafter, referred to as a reference signal) to the input terminal 67 via the capacitor 43.

The load transistor 61 and the load transistor 62 of the differential amplifier 42 constitute a current mirror circuit.

Specifically, the load transistor 61 is connected in series between a power supply of the potential VDD (hereinafter, referred to as a power supply VDD) and the input transistor 63. That is, the source of the load transistor 61 is connected to the power supply VDD, and the drain of the load transistor 61 is connected to the drain of the input transistor 63. Furthermore, the gate of the load transistor 61 is connected to the gate of the load transistor 62 and is connected to the drain of the load transistor 61. That is, the load transistor 61 is diode-connected.

The load transistor 62 is connected in series between the power supply VDD and the input transistor 64. That is, the source of the load transistor 62 is connected to the power supply VDD, and the drain of the load transistor 62 is connected to the drain of the input transistor 64. Note that the load transistor 62 is non-diode-connected.

The input transistor 63 is connected in series between the load transistor 61 and the constant current source 65. That is, the drain of the input transistor 63 is connected to the drain of the load transistor 61 as described above, and the source of the input transistor 63 is connected to the constant current source 65. The gate of the input transistor 63 is connected to the input terminal 66, and a cell potential signal from the read electrode 41 is input thereto. Note that since the load transistor 61 is diode-connected, no amplification gain is applied to the input transistor 63.

The input transistor 64 is connected in series between the load transistor 62 and the constant current source 65. That is, the drain of the input transistor 64 is connected to the drain of the load transistor 62 as described above, and the source of the input transistor 64 is connected to the constant current source 65. The gate of the input transistor 63 is connected to the input terminal 67, and a reference signal from the reference electrode 12 is input thereto via the capacitor 43. Note that since the load transistor 62 is non-diode-connected, an amplification gain is applied to the input transistor 64.

The constant current source 65 is connected to a power supply of the potential VSS (hereinafter, referred to as a power supply VSS). The potential VSS is, for example, ground (GND).

The output terminal 68 is connected to a connection point between the drain of the load transistor 62 and the drain of the input transistor 64.

As described above, the differential amplifier 42 is a differential amplifier in which the current mirror circuit including the load transistor 61 and the load transistor 62 is used as a load resistor. Furthermore, the differential amplifier 42 amplifies a potential difference between the cell potential signal input to the input terminal 66 and the reference signal input to the input terminal 67, and outputs an output signal indicating the amplified potential difference from the output terminal 68.

The capacitor 43 is connected between the reference electrode 12 and the input terminal 67 of the differential amplifier 42. The capacitor 43 cancels noise components mixed in phase at the read electrode 41 and the reference electrode 102. Furthermore, the capacitor 43 works as a sampling capacitor that samples and holds a potential that is the operating point of the differential amplifier 42.

The capacitor 44 is connected between the input terminal 67 and the output terminal 68 of the differential amplifier 42. Therefore, an output signal output from the output terminal 68 is fed back to the input terminal 67 as an input signal to form a closed loop, and the capacitor 44 is connected in the closed loop.

The reset switch 45 is connected between the output terminal 68 and the input terminal 67 of the differential amplifier 42 in parallel with the capacitor 44. The reset switch 45 short-circuits between the input terminal 67 and the output terminal 68 on the basis of a reset signal Reset supplied from a control circuit (not illustrated). Thus, a reset operation of the operating point of the differential amplifier 42 is performed. That is, the currents flowing through the load transistor 61 and the load transistor 62 of the differential amplifier 42 are balanced to make the potential difference between the input signals of the differential amplifier 42 zero (Vin(+)−Vin(−)=0), and the potential of the reference electrode 12 in this state is sampled and held in the capacitor 43 as the operating point of the differential amplifier 42.

The switch 46 outputs an output signal from the differential amplifier 42 to a vertical signal line 14 as a sensor signal under the control using a selection signal input via a sensor drive line 13. Specifically, in a case where the selection signal is input, the switch 46 is on and outputs the sensor signal to the vertical signal line 14. Thus, a value indicating the potential of the biological cells is sampled. On the other hand, in a case where the selection signal is not input, the switch 46 is off and does not output the sensor signal to the vertical signal line 14.

Figure 2:
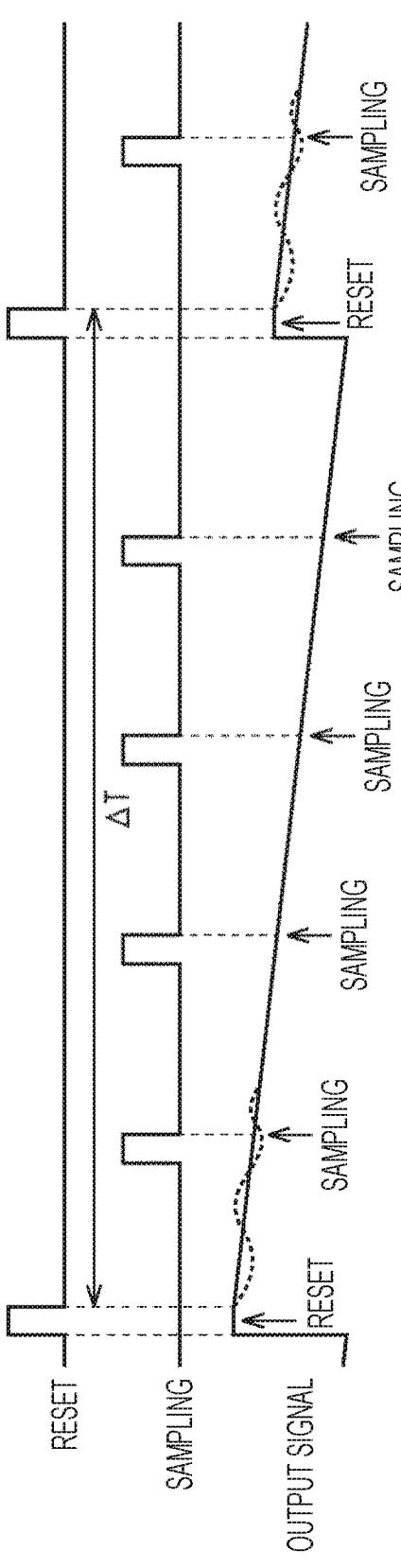
FIG. 2 is a diagram illustrating an example of the timing of a reset operation and a sampling operation of the sensor in FIG. 1.

FIG. 2 illustrates an example of the timing of the reset operation of the sensor 11 and the sampling operation of the potential of the biological cells.

As described above, in the sensor 11, the operating point of the differential amplifier 42 is sampled and held in the capacitor 43 by the reset operation. However, the potential sampled and held in the capacitor 43 gradually decreases due to the leakage current. Therefore, even if the cell potential signal does not change, the output signal of the differential amplifier 42 gradually decreases, and the values of the sensor signal output from the sensor 11 (sample values) vary.

Therefore, it is necessary to periodically perform the reset operation of the operating point to refresh the sensor 11.

Meanwhile, the sensor 11 cannot detect a signal in a frequency band lower than the cutoff frequency based on a period ΔT of the reset operation (hereinafter, referred to as a reset period ΔT).

Figure 3:
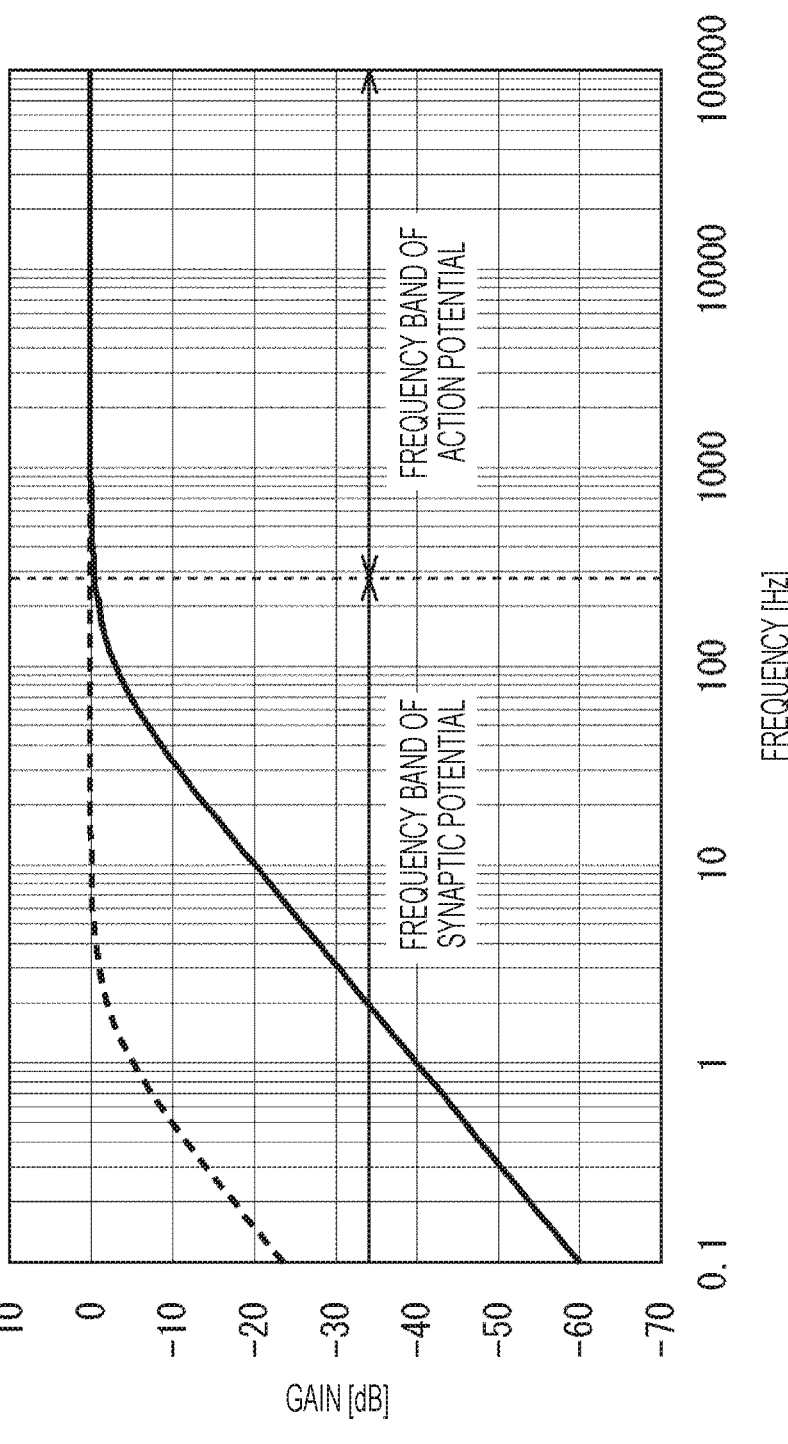
FIG. 3 is a graph illustrating an example of frequency characteristic of a differential amplifier.

FIG. 3 illustrates an example of frequency characteristic of the differential amplifier 42 in a case where the cutoff frequency fc based on the reset period ΔT is 100 Hz. The horizontal axis represents the frequency (Hz), and the vertical axis represents the gain (dB). The frequency characteristic of the differential amplifier 42 is indicated by a solid line.

There are generally two types of potentials generated by biological cells: an action potential obtained by signals in a frequency band of 300 Hz or higher and a synaptic potential (also referred to as a local field potential (LFP)) obtained by signals in a frequency band of 300 Hz or lower. In a case where the cutoff frequency fc is 100 Hz, an action potential in a high frequency band can be measured while a synaptic potential in a low frequency band cannot be measured, so that measurement accuracy is deteriorated.

Furthermore, as indicated by a broken line in the waveform of the output signal in FIG. 2, immediately after the reset operation, the output signal fluctuates due to the influence of on/off of the reset switch 45. Therefore, noise occurs in the sensor signal sampled immediately after the reset operation.

Moreover, it is necessary to correct the slope of the output signal due to the leakage current by signal processing in a subsequent stage, and the processing load in the subsequent stage increases.

On the other hand, the present disclosure is directed to improve the measurement accuracy of the potential of a solution such as a culture solution containing biological cells.

2. First Embodiment

Figure 4:
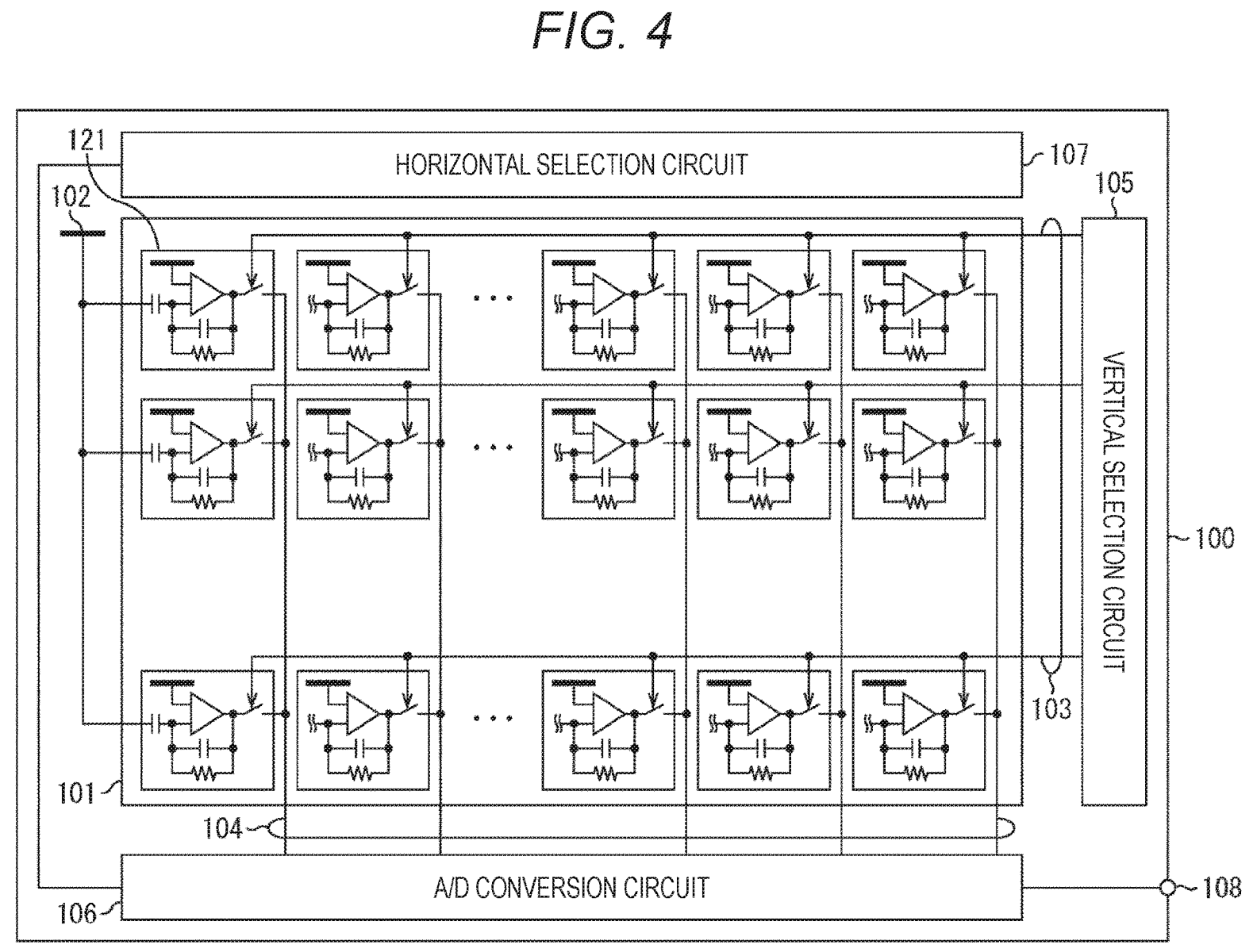

Next, a first embodiment of the present disclosure will be described with reference to FIGS. 4 to 7.
<Configuration Example of Cell Potential Measuring Device 100>
FIG. 4 is a circuit diagram illustrating a configuration example of a cell potential measuring device 100 to which the present disclosure is applied.

The cell potential measuring device 100 is a semiconductor device (semiconductor device) in which a sensing unit 101, a reference electrode 102, sensor drive lines 103, vertical signal lines 104, a vertical selection circuit 105, an A/D conversion circuit 106, a horizontal selection circuit 107, and an output terminal 108 are formed on a semiconductor substrate (chip) (not illustrated) using a CMOS integration technology.

In the sensing unit 101 of the cell potential measuring device 100, sensors 121 each for reading an electrochemical potential of a culture solution containing biological cells are two-dimensionally arranged in an array (matrix). Furthermore, in the sensing unit 101, the sensor drive lines 103 each are formed for one row, in the horizontal direction, of the sensors 121 arranged in an array, and the vertical signal lines 104 each are formed for one column, in the vertical direction, of the sensors 121.

The reference electrode 102 corresponds to the reference electrode 12 in FIG. 1, and is disposed at a position away from the biological cells in the culture solution to read a reference potential of the culture solution. The reference electrode 102 supplies a reference signal, which is an electric signal indicating the read reference potential, to each sensor 121.

The vertical selection circuit 105 drives the sensors 121 of the sensing unit 101 row by row, for example. Specifically, to output terminals (not illustrated) corresponding to the respective rows of the vertical selection circuit 105, one ends of the sensor drive lines 103 are connected. The vertical selection circuit 105 sequentially selects the rows so as to sequentially read sensor signals from the sensors 121 row by row, and outputs a selection signal or the like from the output terminal connected to the sensor drive line 103 of the selected row. As a result, the sensors 121 in the selected row supply output signals indicating the potential of the culture solution to the vertical signal lines 104 as sensor signals.

The A/D conversion circuit 106 includes a signal processing circuit for each column of the sensing unit 101. Each signal processing circuit of the A/D conversion circuit 106 performs signal processing such as A/D conversion processing on the sensor signal output from the corresponding sensor 121 in the selected row via the vertical signal line 104. The A/D conversion circuit 106 outputs, via the output terminal 108, the sensor signal after the signal processing, obtained by the signal processing circuit selected according to the selective scanning of the horizontal selection circuit 107.

Figure 5:
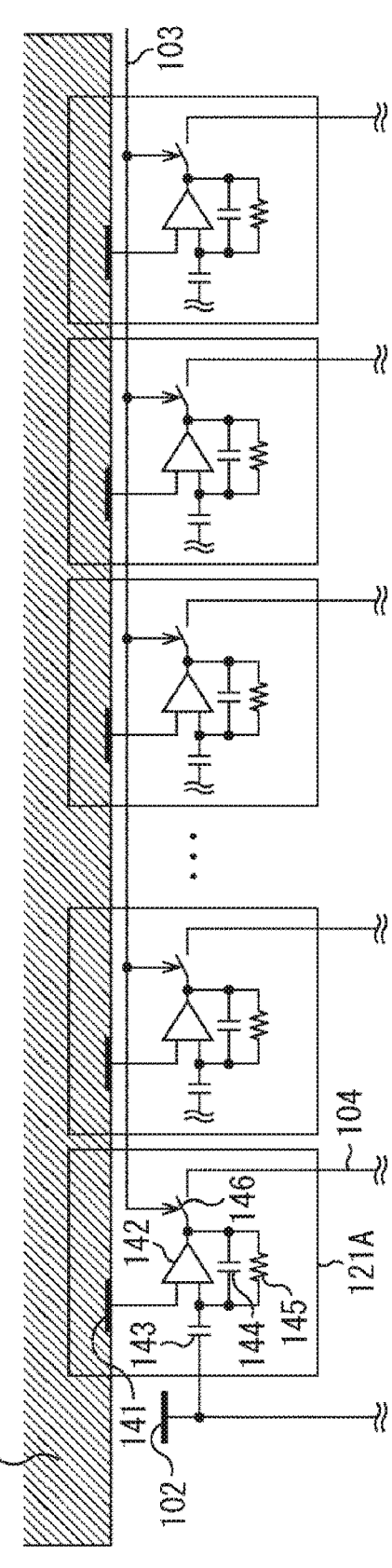
FIG. 5 is a circuit diagram illustrating a configuration example of a sensor in FIG. 4.

The horizontal selection circuit 107 sequentially selects the signal processing circuits of the A/D conversion circuit 106. By the selective scanning by the horizontal selection circuit 107, the sensor signals subjected to the signal processing by the respective signal processing circuits of the A/D conversion circuit 106 are sequentially output to the output terminal 108.
<First Embodiment of Sensor 121>
FIG. 5 is a diagram illustrating a configuration example of sensors 121A, each of which is a first embodiment of the sensor 121 in FIG. 4. Note that in FIG. 4, only the sensors 121A in one row are illustrated for convenience of description.

Each of the sensors 121A includes a read electrode 141, a differential amplifier 142, a capacitor 143, a capacitor 144, a high resistor 145, and a switch 146.

The read electrode 141 corresponds to the read electrode 41 of the sensor 11 in FIG. 1. The read electrode 141 is disposed in a culture solution C containing biological cells. The read electrode 141 reads the potential of the culture solution C as the potential of the biological cells contained in the culture solution C, and outputs a cell potential signal, which is an electrical signal indicating the read potential.

To the differential amplifier 142, a cell potential signal is input from the read electrode 141. Furthermore, to the differential amplifier 142, a reference signal is input from the reference electrode 102 via the capacitor 143. The differential amplifier 142 outputs an output signal obtained by amplifying the potential difference between the two input signals.

The capacitor 143 corresponds to the capacitor 43 of the sensor 11 in FIG. 1, and is connected between the reference electrode 102 and the input terminal of the differential amplifier 142.

The capacitor 144 corresponds to the capacitor 44 of the sensor 11 in FIG. 1, and is connected between the input terminal, on the side of the reference electrode 102, and the output terminal of the differential amplifier 142.

The high resistor 145 is connected between the input terminal, on the side of the reference electrode 102, of the differential amplifier 142, and the output terminal, in parallel with the capacitor 144. The high resistor 145 includes, for example, a resistance element having a very high resistance value (tor example, 1 GΩ or higher) using polysilicon or metal wiring used in a semiconductor process.

The switch 146 corresponds to the switch 46 of the sensor 11 in FIG. 1. The switch 146 outputs an output signal from the differential amplifier 142 to a vertical signal line 104 as a sensor signal under the control using a selection signal input by the sensor drive line 103 in FIG. 4. Specifically, in a case where the selection signal is input, that is, in a case where the row on which the sensor 121 is disposed is the selected row, the switch 146 is on and outputs the sensor signal to the vertical signal line 104. On the other hand, in a case where the selection signal is not input, that is, in a case where the row in which the sensor 121 is disposed is not the selected row, the switch 146 is off and does not output the sensor signal to the vertical signal line 104.

<Detailed Configuration Example of Sensor 121A>

Figure 6:
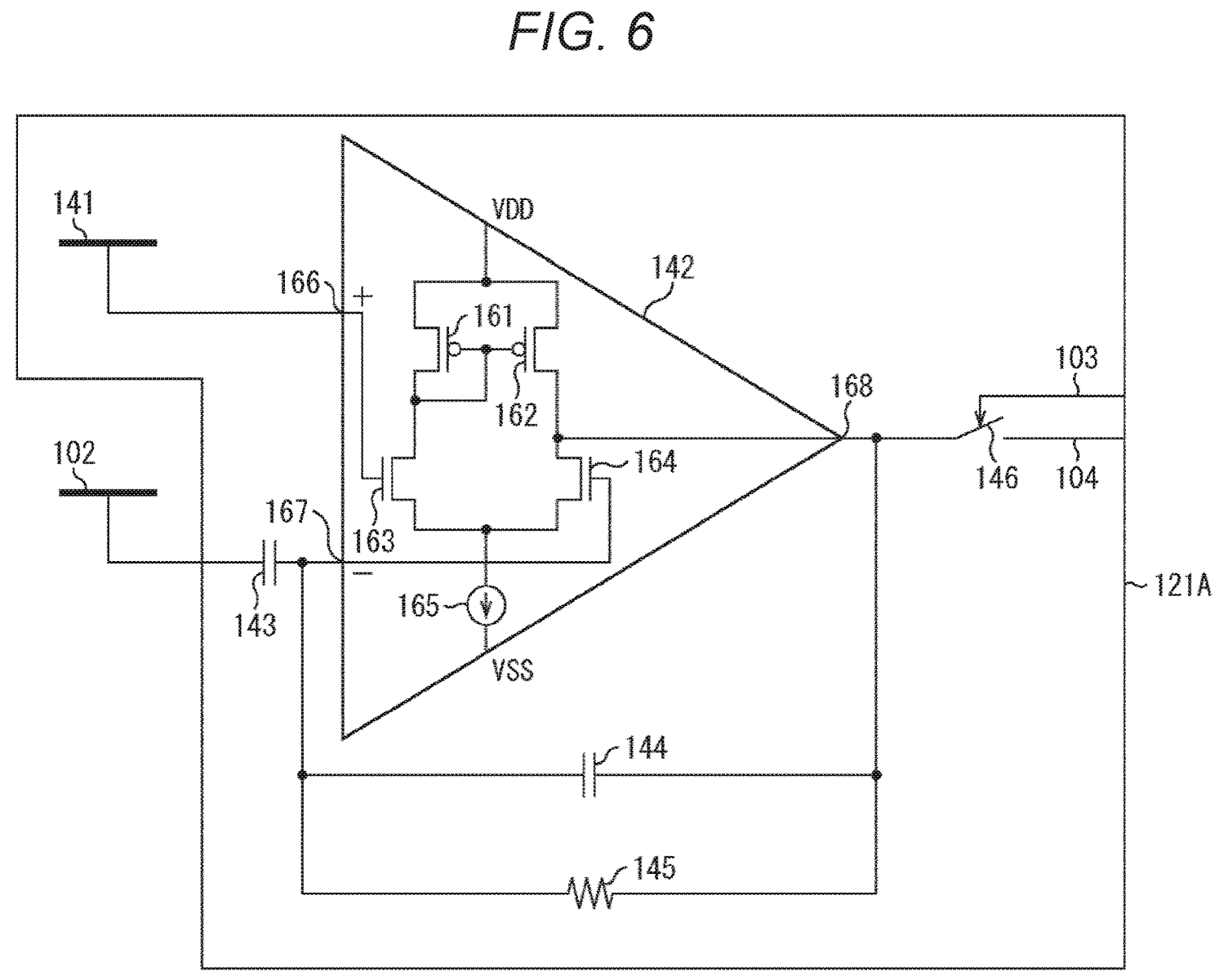

FIG. 6 is a circuit diagram illustrating the configuration of the sensor 121A in FIG. 5 in more detail.

As described above, the sensor 121A includes the read electrode 141, the differential amplifier 142, the capacitor 143, the capacitor 144, the high resistor 145, and the switch 146. The differential amplifier 142 includes a load transistor 161, a load transistor 162, an input transistor 163, an input transistor 164, a constant current source 165, an input terminal 166, an input terminal 167, and an output terminal 168.

The sensor 121A is different from the sensor 11 in FIG. 1 only in that the reset switch 45 is replaced with the high resistor 145. That is, the read electrode 141 to the capacitor 144 and the switch 146 are configured similarly to the read electrode 41 to the capacitor 44 and the switch 46 in FIG. 1. Furthermore, the load transistors 161 to the output terminal 168 of the differential amplifier 142 are configured similarly to the load transistor 161 to the output terminal 68 of the differential amplifier 42 in FIG. 1.

Therefore, the sensor 121A can achieve the effect provided by the single feedback auto-zero differential amplifier, similarly to the sensor 11 in FIG. 1.

That is, in the differential amplifier 142 of the sensor 121A, a closed loop in which an output signal is fed back as an input signal is formed, so that it is possible to suppress an amplification gain and widen a signal input range as compared with an open loop differential amplifier.

Furthermore, in the differential amplifier 142, a circuit or the like is not inserted between the read electrode 141 and the input transistor 163, so that an amplification gain of 1 or less is not applied to the read signal, and signal/noise (S/N) is not deteriorated.

Moreover, in the differential amplifier 142, the output signal is not fed back to the read electrode 141. Therefore, it is possible to prevent the fluctuation of the potential of the read electrode 141 due to the feedback of the output signal from affecting the activity of the biological cells and then prevent hindering accurate measurement of the action potential of the biological cells.

In addition, by replacing the reset switch 45 with the high resistor 145, the input on the side of the input terminal 167 of the single feedback differential amplifier 142 is biased by the high resistor 145. Therefore, for example, as described, for example, in "R. R. Harrison, C. Charles, 'A low-power low-noise CMOS amplifier for neural recording applications,' IEEE J. Solid-State Circuits, vol. 38, pp. 958-965, 2003", a potential in a low frequency band can be measured.

Specifically, the cutoff frequency fc of the differential amplifier 142 is obtained by the following equation (1).

$$fc = 1/(2\pi \times R \times Cgd) \tag{1}$$

Note that R represents the resistance value of the high resistor 145, and Cgd represents the capacitance of the capacitor 144.

For example, in a case where Cgd=10 F is satisfied, the cutoff frequency fc=1.5 Hz is obtained by setting R=10 TΩ. Therefore, as indicated by the broken line graph in FIG. 3 described above, the frequency characteristic, in the lower frequency region, of the differential amplifier 142 is improved as compared with the frequency characteristic of the differential amplifier 42 (FIG. 1) indicated by the solid line. As a result, it is possible to measure the synaptic potential in a low frequency band, so that the measurement accuracy of the potential of the biological cells is improved.

Furthermore, since the fluctuation of the output signal due to the leakage current of the capacitor 143 is suppressed, the reset operation becomes unnecessary. As a result, the periodic fluctuation of the output signal due to the reset operation is prevented, so that the measurement accuracy of the potential of the biological cells is improved.

Figure 7:
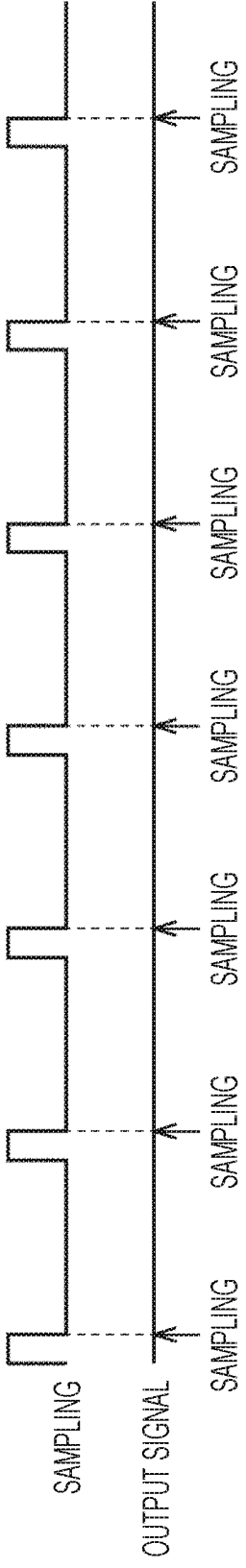
FIG. 7 is a diagram illustrating an example of the timing of a reset operation and a sampling operation of the sensor in FIG. 6.

For example, FIG. 7 illustrates an example of the timing of the sampling operation of the potential of the biological cells by the sensor 121A. As can be seen, the fluctuation of the output signal is suppressed without performing the reset operation, so that the measurement accuracy of the potential of the biological cells is improved.

3. Second Embodiment

Next, a second embodiment of the present disclosure will be described with reference to FIG. 8.

<Second Embodiment of Sensor 121>

Figure 8:
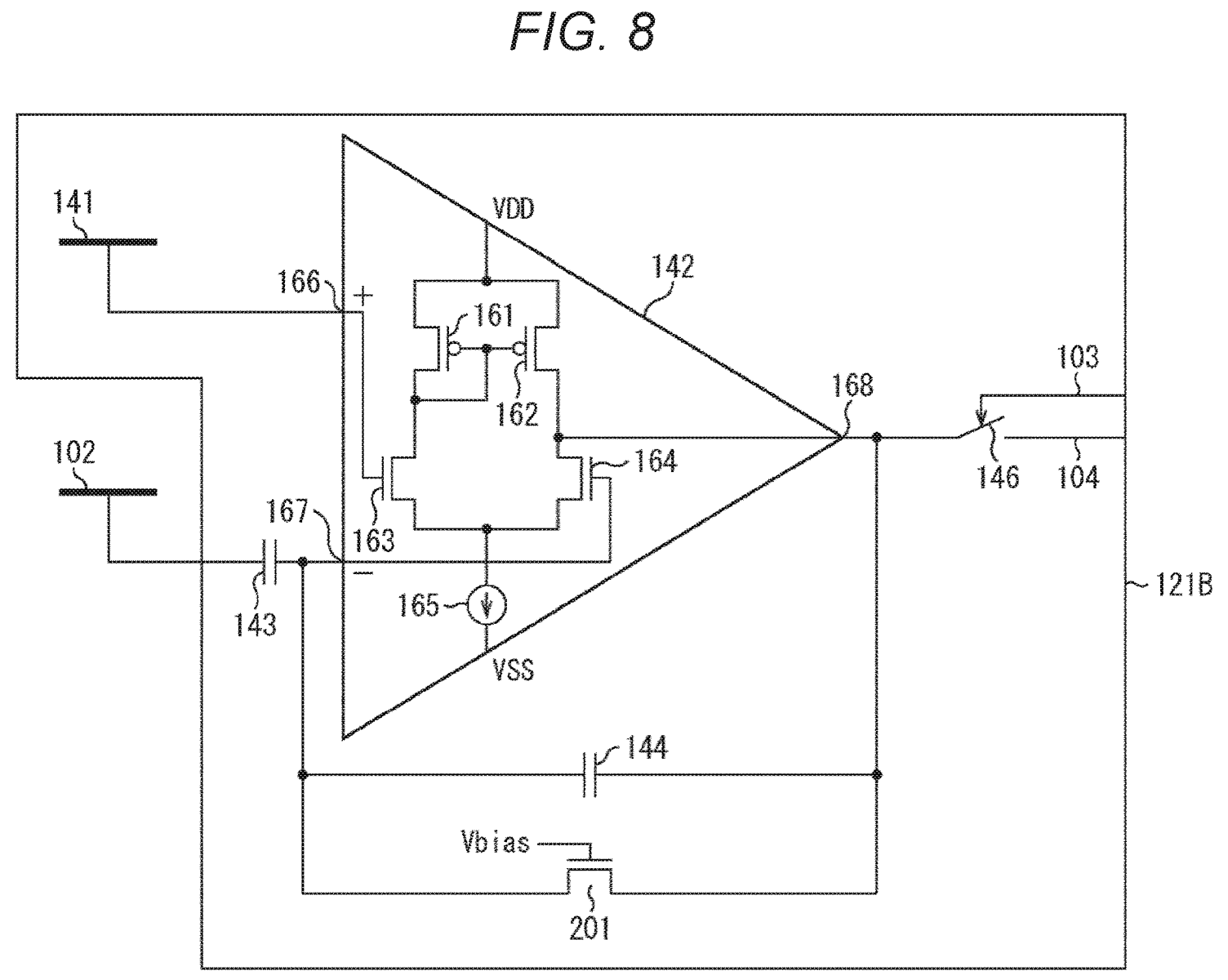

FIG. 8 is a circuit diagram illustrating a configuration example of a sensor 121B, each of which is a second embodiment of the sensor 121 in FIG. 4. Note that in the figure, parts corresponding to those of the sensor 121A in FIG. 6 are denoted by the same reference numerals, and the description thereof will not be provided as appropriate.

The sensor 121B is different from the sensor 121A in that a transistor 201 including an nMOS transistor is provided instead of the high resistor 145.

The transistor 201 is connected between the input terminal 167 and the output terminal 168 of the differential amplifier 142, in parallel with the capacitor 144. A bias voltage Vbias lower than the threshold voltage of the transistor 201 is applied to the gate of the transistor 201. Therefore, the transistor 201 operates in the subthreshold region, and the transistor 201 can be used as a high resistor.

Note that the bias voltage Vbias may be generated by a bias generation circuit (not illustrated) inside the sensing unit 101, or may be generated by a voltage supply device outside the sensing unit 101 and supplied.

The resistance value of the transistor 201 can be freely set by, for example, changing the bias voltage Vbias applied to the transistor 201. Therefore, the frequency characteristic of the differential amplifier 142 can be freely changed from the outside. For example, in the differential amplifier 142, an unnecessary frequency band can be cut to narrow down output signals to acquire output signals in a necessary frequency band, so that improvement in S/N (noise reduction) can be achieved.

4. Third Embodiment

Next, a third embodiment of the present disclosure will be described with reference to FIG. 9.
<Third Embodiment of Sensor 121>

Figure 9:
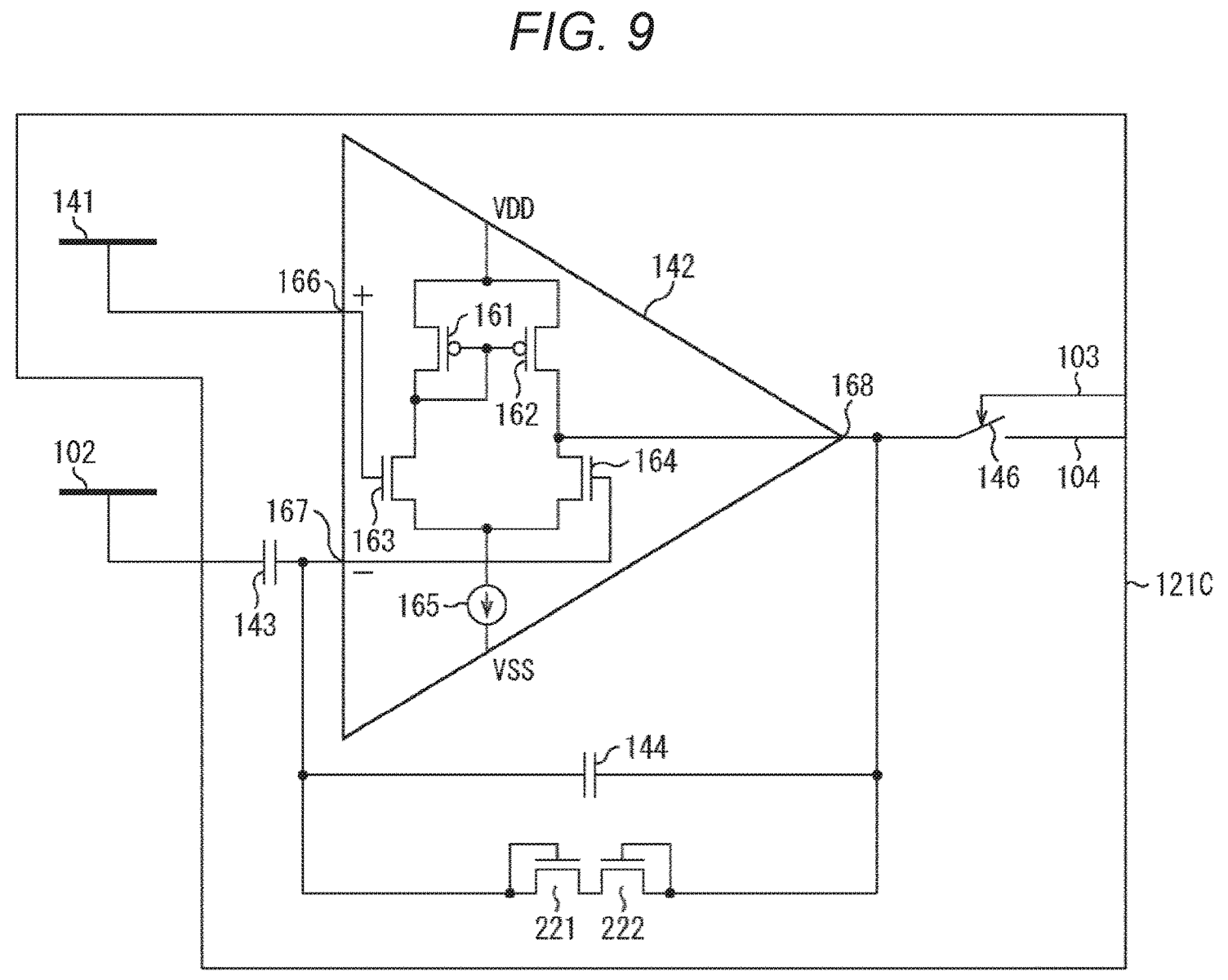

FIG. 9 is a diagram illustrating a configuration example of sensors 121C, each of which is a third embodiment of the sensor 121 in FIG. 4. Note that in the figure, parts corresponding to those of the sensor 121A in FIG. 6 are denoted by the same reference numerals, and the description thereof will not be provided as appropriate.

The sensor 121C is different from the sensor 121A in that a transistor 221 and a transistor 222 each including an nMOS transistor are provided instead of the high resistor 145.

The transistor 221 and the transistor 222 are connected in series, and are connected in parallel with the capacitor 144 between the output terminal 168 and the input terminal 167. Furthermore, the transistor 221 and the transistor 222 are diode-connected such that directions in which current flows are opposite to each other.

Then, in a case where the voltage difference between the drain and the source of each of the transistor 221 and the transistor 222 is less than the threshold value, only a very small current flows through the transistor 221 and the transistor 222. Therefore, the transistor 221 and the transistor 222 can be used as a high resistor.

Therefore, a high resistor can be realized without supplying a bias voltage from the outside.

5. Fourth Embodiment

Next, a fourth embodiment of the present disclosure will be described with reference to FIG. 10.
<Configuration Example of Sensing Unit 301>

FIG. 10 illustrates a configuration example of a sensing unit 101 that is a modification of the sensing unit 301 in FIG. 4.

In the sensing unit 301, the sensor 121A in FIG. 6 is divided into a read cell 321 and a reference cell 322, and the current mirror circuit and the constant current source included in the sensor 121A are shared in each column.

Specifically, the sensing unit 301 includes a read cell area 311 and a reference cell area 312 separated from each other. The read cell area 311 and the reference cell area 312 are arranged side by side in the vertical direction. In the read cell area 311, the read cells 321 are two-dimensionally arranged in an array. In the reference cell area 312, reference cells 341 are two-dimensionally arranged in an array. The arrangement of the read cells 321 in the read cell area 311 is similar to the arrangement of the reference cells 341 in the reference cell area 312, and the read cells 321 and the reference cells 341 arranged at positions corresponding to each other operate in cooperation.

Furthermore, a load transistor 313 and a load transistor 314 each including a pMOS transistor, and a constant current source 315 are provided for each column of the areas including the read cell area 311 and the reference cell area 312.

The load transistor 313 and the load transistor 314 correspond to the load transistor 161 and the load transistor 162 of the sensor 121A in FIG. 6, and constitute a current mirror circuit. The source of the load transistor 313 is connected to the power supply VDD, the drain is connected to each of the read cells 321 arranged in the same column, and the gate is connected to the gate of the load transistor 314. Furthermore, the load transistor 313 is diode-connected. That is, the drain and the gate of the load transistor 313 are connected. The source of the load transistor 314 is connected to the power supply VDD, and the drain is connected to each of the reference cells 341 arranged in the same column. Note that the load transistor 314 is non-diode-connected.

The constant current source 315 is connected between the read cells 321 and the reference cells 341 arranged in the same column, and the power supply VSS (not illustrated).

Each read cell 321 includes a read electrode 331, an input transistor 332 including an nMOS transistor, and a switch 333 to constitute a read circuit of the potential of the biological cells. The read electrode 331 and the input transistor 332 correspond to the read electrode 141 and the input transistor 163 of the sensor 121A in FIG. 6.

The drain of the input transistor 332 is connected to the drain of the load transistor 313 via the switch 333, the source is connected to the constant current source 315, and the gate is connected to the read electrode 331.

Each reference cell 322 includes a capacitor 351, an input transistor 352 including an nMOS transistor, a capacitor 353, a high resistor 354, and a switch 355, and constitutes a reading circuit of the reference potential. The capacitor 351, the input transistor 352, the capacitor 353, and the high resistor 354 correspond to the capacitor 143, the input transistor 164, the capacitor 144, and the high resistor 145 of the sensor 121A in FIG. 6.

The drain of the input transistor 352 is connected to the drain of the load transistor 314 via the switch 355, the source is connected to the constant current source 315, and the gate is connected to a reference electrode (not illustrated) via the capacitor 351. The capacitor 353 is connected between drain of the load transistor 314 and the gate of the input transistor 352. The high resistor 354 is connected in parallel with the capacitor 353 between the drain of the load transistor 314 and the gate of the input transistor 352.

The switch 333 of each read cell 321 and the switch 355 of each reference cell 322 are turned on or off under the control using a selection signal input via a sensor drive line (not illustrated). For example, when a selection signal is input to the switch 333 of each of the read cells 321 and the switch 355 of each of the reference cells 322 in the selected row, the switch 333 and the switch 355 are turned on. Therefore, the read cell 321 and the reference cell 341 in the selected row, the load transistor 313, the load transistor 314, and the constant current source 315 arranged in the same column constitute a circuit similar to the sensor 121A in FIG. 6. Furthermore, the input transistor 332 of the read cell 321 and the input transistor 352 of the reference cell 341 in the selected row, the load transistor 313, and the load transistor 314 arranged in the same column constitute a circuit similar to the differential amplifier 142 in FIG. 6.

Then, a sensor signal (output signal) is output from a connection point between the drain of the load transistor 314 and the drain of the input transistor 352 of the reference cell 341 in the selected row.

The sensing unit 301 can achieve the following effects in addition to the effects achieved by the sensing unit 101 and each sensor 121A in FIG. 4 described above.

For example, the current mirror circuit and the constant current source 315 are shared, so that the sensing unit 301 can be made smaller. Alternatively, by increasing the number of the read cells 321 and the reference cells 341, the resolution of the potential of the biological cells (the number of the measurement points) can be increased.

Furthermore, the read cell area 311 and the reference cell area 312 are separated, so that it is possible to reduce the area of the read cell 321 to increase the spatial resolution of the cell potential while the size of the input transistor 332 is increased, and reduce noise.

Moreover, the addition of the high resistor 354 does not affect each read cell 321, and each read cell 321 is constituted of only three elements of the read electrode 331, the input transistor 332, and the switch 333. Therefore, the area of each read cell 321 can be reduced, and the above-described effect can be further enhanced.

6. Fifth Embodiment

Next, a fifth embodiment of the present disclosure will be described with reference to FIG. 11.

Figure 11:
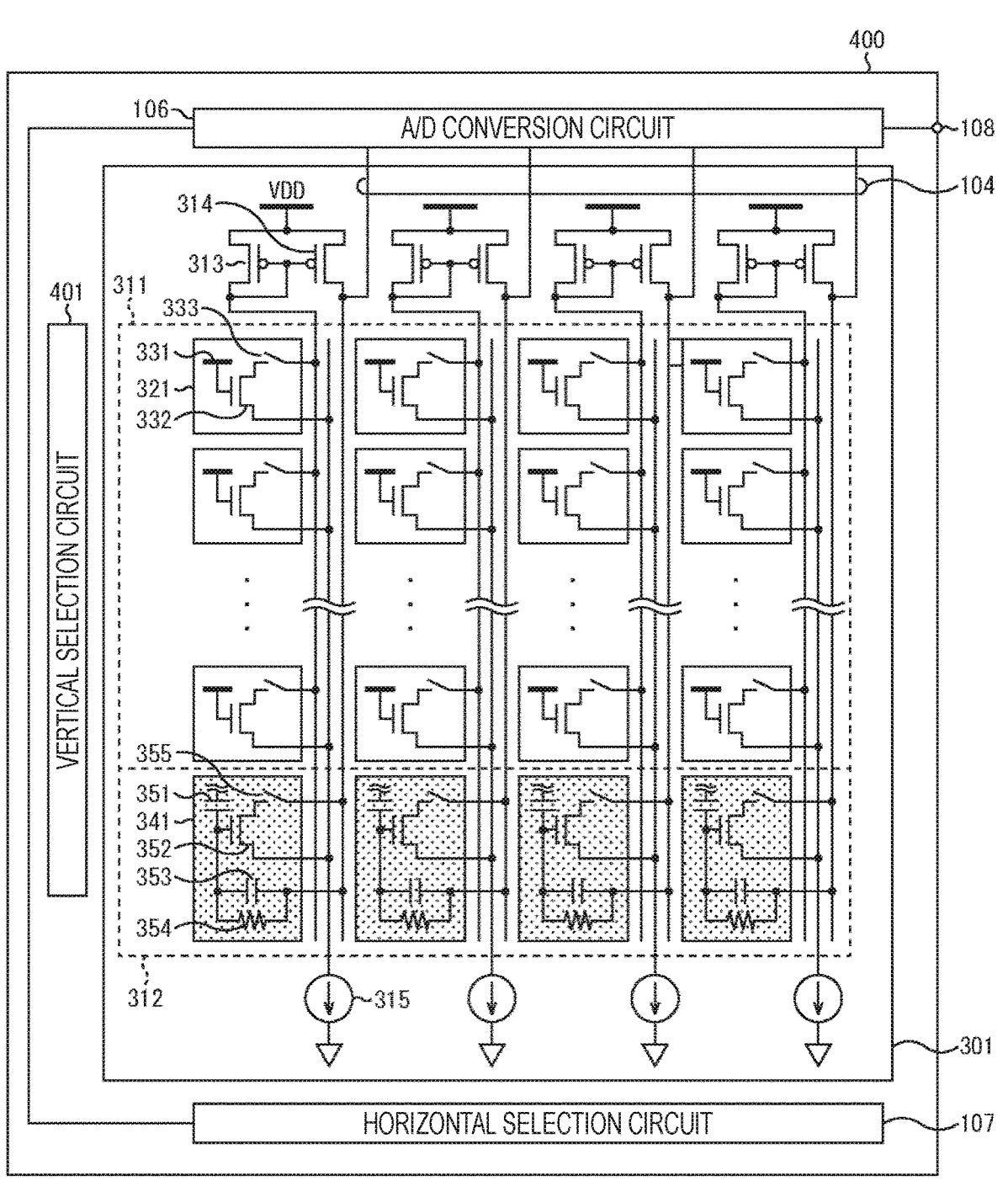
FIG. 11 is a circuit diagram illustrating a configuration example of a second embodiment of a cell potential measuring device to which the present disclosure is applied.

FIG. 11 illustrates a configuration example of a cell potential measuring device 400 that is a modification of the cell potential measuring device 100 in FIG. 4. Note that in the figure, parts corresponding to those of the cell potential measuring device 100 are denoted by the same reference numerals, and the description thereof will not be provided as appropriate.

The cell potential measuring device 400 is the same as the cell potential measuring device 100 in that it includes the reference electrode 102, the vertical signal lines 104, the A/D conversion circuit 106, and the output terminal 108. Note that the reference electrode 102 is not illustrated. On the other hand, the cell potential measuring device 400 is different from the cell potential measuring device 100 in that the sensing unit 301 in FIG. 10 described above and a vertical selection circuit 401 are provided instead of the sensing unit 101 and the vertical selection circuit 105.

Note that although a part of the illustration of the reference cells 341 in the reference cell area 312 of the sensing unit 301 is not provided in this figure, the numbers of rows and columns of the read cells 321 in the read cell area 311 and the numbers of rows and the columns of the reference cells 341 in the reference cell area 312 are the same, respectively.

The vertical selection circuit 401 drives the read cells 321 in the read cell area 311 of the sensing unit 301 and the reference cells 341 in the reference cell area 312 row by row. Specifically, one end of a sensor drive line (not illustrated) is connected to an output terminal (not illustrated) of the vertical selection circuit 401 corresponding to each row of the read cell area 311 and the reference cell area 312.

The vertical selection circuit 105 sequentially selects the rows of the read cell area 311 and the reference cell area 312 so as to sequentially read sensor signals from the read cells 321 row by row, and output selection signals or the like from the output terminal connected to the sensor drive line of the selected rows. Therefore, the switches 333 of the read cells 321 and the switches 355 of the reference cells 341 in the selected row are turned on. As a result, sensor signals are output from connection points between the drains of the load transistors 314 and the drains of the input transistors 352 of the reference cells 341 in the selected row, and are supplied to the A/D conversion circuit 106 via the vertical signal lines 104. Then, a digital sensor signal indicating the potential of the biological cells is output from the A/D conversion circuit 106 to the outside of the cell potential measuring device 400 via the output terminal 108.

In this way, it is possible to output a digital sensor signal to the outside of the cell potential measuring device 400 with low noise at high speed. Furthermore, by sequentially selecting the read cells 321 and the reference cells 341 by the vertical selection circuit 401, it is possible to arrange a large number of read electrodes 331. This makes it possible to measure the potential of the biological cells at a higher resolution in a wider range.

7. Modifications

For example, in the sensor 121A in FIG. 6, the sensor 121B in FIG. 8, and the sensor 121C in FIG. 9, the reference electrode 102 and the capacitor 143 may be eliminated, and a configuration in which the output signal of the differential amplifier 142 is fed back to the input terminal 167 via the capacitor 144 may be formed.

For example, in the sensing unit 301 in FIG. 10 and the cell potential measuring device 400 in FIG. 11, instead of the high resistor 354, a resistance element having a configuration similar to the transistor 201 of the sensor 121B in FIG. 8 or the transistor 221 and the transistor 222 of the sensor 121C in FIG. 9 can be used.

For example, the reference electrode 102 in FIG. 4 and the like may read a reference potential different from the reference potential of the culture solution. For example, the reference electrode 102 may be connected to the ground (GND), and the reference electrode 102 may read the ground as the reference potential.

Similarly, a reference electrode (not illustrated) to which the capacitor 351 in FIG. 10 or the like is connected may read a reference potential different from the reference potential of the culture solution.

8. Others

Note that the effects described in the present specification are merely examples and are not limited, and other effects may be provided.

Furthermore, the embodiments of the present disclosure are not limited to the above-described embodiments, and various modifications can be made without departing from the gist of the present disclosure.

Note that the present disclosure may also have the following configurations.

(1)

A semiconductor device including:

a read electrode that reads a potential of a solution;

a differential amplifier;

a first capacitor connected in series in a loop feeding back an output of the differential amplifier to a second input different from a first input from the read electrode;

a resistance element connected in parallel with the first capacitor; and a second capacitor connected between a reference electrode indicating a reference potential and the second input.

(2)

The semiconductor device according to above-described (1), in which the differential amplifier includes:

a current mirror circuit including a first load transistor that is diode-connected and a second load transistor that is non-diode-connected;

a first input transistor that is connected in series to the first load transistor and that includes a gate connected to the read electrode; and a second input transistor that is connected in series to the second load transistor and that includes a gate connected to the first capacitor.

(3)

The semiconductor device according to above-described (2) including:

a read cell area in which a plurality of read cells each including the read electrode and the first input transistor is arranged in an array; and a reference cell area in which a plurality of reference cells each including the second input transistor is arranged in an array, the reference cell area being separated from the read cell area.

(4)

The semiconductor device according to above-described (3), in which the reference cell includes:

the first capacitor;

the resistance element; and the second capacitor connected between the reference electrode and the gate of the second input transistor.

(5)

The semiconductor device according to above-described (3) or (4), in which the current mirror circuit is provided for each column of an area including the read cell area and the reference cell area.

(6)

The semiconductor device according to above-described (5) further including:

a vertical selection circuit that selects the read cells and the reference cells row by row, and causes the read cell and the reference cell in the selected row and the current mirror circuit in a same column to constitute the differential amplifier.

(7)

The semiconductor device according to any one of above-described (2) to (6), in which an output signal is output from a connection point between the second load transistor and the second input transistor.

(8)

The semiconductor device according to above-described (1), in which the differential amplifier includes:

a first input terminal;

a second input terminal; and an output terminal, in which the read electrode is connected to the first input terminal, the first capacitor is connected between the second input terminal and the output terminal, the resistance element is connected in parallel with the first capacitor between the second input terminal and the output terminal, and the second capacitor is connected between the reference electrode and the second input terminal.

(9)

The semiconductor device according to above-described (8), in which the differential amplifier includes:

a current mirror circuit including a first load transistor that is diode-connected and a second load transistor that is non-diode-connected;

a first input transistor that is connected in series to the first load transistor and that includes a gate connected to the first input terminal; and a second input transistor that is connected in series to the second load transistor and that includes a gate connected to the second input terminal.

(10)

The semiconductor device according to above-described (9), in which the output terminal is connected to a connection point between the second load transistor and the second input transistor.

(11)

The semiconductor device according to any one of above-described (1) to (10), in which the resistance element includes metal wiring or polysilicon.

(12)

The semiconductor device according to any one of above-described (1) to (10), in which the resistance element includes a transistor including a gate to which a bias voltage that operates the transistor in a subthreshold region is applied.

(13)

The semiconductor device according to any one of above-described (1) to (10), in which the resistance element includes:

a first transistor that is diode-connected; and a second transistor that is diode-connected and connected in series to the first transistor so that a direction in which current flows is opposite to that in the first transistor.

(14)

The semiconductor device according to above-described (1), in which the resistance element is 1 GΩ or higher.

(15)

The semiconductor device according to any one of above-described (1), (2), and (8) to (14), in which sensors each including the read electrode, the differential amplifier, the first capacitor, the resistance element, and the second capacitor are arranged in an array.

(16)

The semiconductor device according to any one of above-described (1) to (15), in which the reference potential is a reference potential of the solution or ground.

(17)

A cell potential measuring device including:

a read electrode that reads a potential of a cell contained in a solution;

a differential amplifier;

a first capacitor connected in series in a loop feeding back an output of the differential amplifier to a second input different from a first input from the read electrode;

a resistance element connected in parallel with the first capacitor; and a second capacitor connected between a reference electrode indicating a reference potential and the second input.

REFERENCE SIGNS LIST

100 Cell potential measuring device
101 Sensing unit
102 Reference electrode
105 Vertical selection circuit
106 A/D conversion circuit
107 Horizontal selection circuit
121 and 121A to 121C Sensor
141 Read electrode
142 Differential amplifier
143, 144 Capacitor
145 High resistor 146 Switch
161, 162 Load transistor
163, 164 Input transistor
166, 167 Input terminal
168 Output terminal
201, 221, 222 Transistor
301 Sensing unit
311 Read cell area
312 Reference cell area
313, 314 Load transistor
321 Read cell
331 Read electrode
332 Input transistor
341 Reference cell
351 Capacitor
352 Input transistor
353 Capacitor
354 High resistor
400 Cell potential measuring device
401 Vertical selection circuit

The invention claimed is:

1. A semiconductor device, comprising:
a read electrode configured to read a potential of a solution;
a differential amplifier including a first input terminal, a second input terminal, and an output terminal, wherein
the first input terminal is configured to receive a first input indicating the read potential,
the second input terminal is configured to receive a second input, and
the output terminal is configured to provide an output of the differential amplifier;
a first capacitor connected with the differential amplifier in series in a loop, wherein the loop feeds back the output of the differential amplifier to the second input terminal of the differential amplifier;
a resistance element connected in parallel with the first capacitor; and
a second capacitor connected between a reference electrode and the second input terminal, wherein the reference electrode indicates a reference potential.

2. The semiconductor device according to claim 1, wherein the differential amplifier further comprises:
a current mirror circuit, wherein
the current mirror circuit includes a first load transistor and a second load transistor,
the first load transistor is a diode-connected transistor, and
the second load transistor is a non-diode-connected transistor;
a first input transistor connected in series to the first load transistor, wherein the first input transistor includes a first gate terminal connected to the read electrode; and
a second input transistor connected in series to the second load transistor, wherein the second input transistor includes a second gate terminal connected to the first capacitor.

3. The semiconductor device according to claim 2, wherein
the semiconductor device is a part of a sensor circuit,
the sensor circuit comprises:
a read cell area that includes a plurality of read cells arranged in a first array, wherein a candidate read cell of the plurality of read cells includes the read electrode and the first input transistor; and
a reference cell area that includes a plurality of reference cells arranged in a second array, wherein a candidate reference cell of the plurality of reference cells includes the second input transistor, and
the reference cell area is separated from the read cell area.

4. The semiconductor device according to claim 3, wherein the candidate reference cell further comprises:
the first capacitor;
the resistance element; and
the second capacitor, wherein the second capacitor is connected between the reference electrode and the second gate terminal of the second input transistor.

5. The semiconductor device according to claim 3, wherein
a candidate column of a sensor area of the sensor circuit includes the current mirror circuit, and
the sensor area includes the read cell area and the reference cell area.

6. The semiconductor device according to claim 5, further comprising a vertical selection circuit configured to select a first read cell of the plurality of read cells and a first reference cell of the plurality of reference cells, wherein
the first read cell and the first reference cell are in the candidate column of the sensor area, and
the first read cell, the first reference cell, and the current mirror circuit of the candidate column constitute the differential amplifier.

7. The semiconductor device according to claim 2, wherein an output signal is output from a connection point between the second load transistor and the second input transistor.

8. The semiconductor device according to claim 1, wherein
the read electrode is connected to the first input terminal,
the first capacitor is connected between the second input terminal and the output terminal, and
the resistance element is connected between the second input terminal and the output terminal.

9. The semiconductor device according to claim 1, wherein the differential amplifier further comprises:
a current mirror circuit, wherein
the current mirror circuit includes a first load transistor and a second load transistor,
the first load transistor is a diode-connected transistor, and
the second load transistor is a non-diode-connected transistor;
a first input transistor connected in series to the first load transistor, wherein the first input transistor includes a first gate terminal connected to the first input terminal; and
a second input transistor connected in series to the second load transistor, wherein the second input transistor includes a second gate terminal connected to the second input terminal.

10. The semiconductor device according to claim 9, wherein the output terminal is connected to a connection point between the second load transistor and the second input transistor.

11. The semiconductor device according to claim 1, wherein the resistance element includes one of a metal wiring or polysilicon.

12. The semiconductor device according to claim 1, wherein the resistance element includes a transistor, wherein the transistor is configured to operate in a subthreshold region based on application of a bias voltage to a gate terminal of the transistor.

13. The semiconductor device according to claim 1, wherein the resistance element comprises:

a first diode-connected transistor; and a second diode-connected transistor, wherein the second diode-connected transistor is connected in series to the first diode-connected transistor, and a direction of current flow through the second diode-connected transistor is opposite to a direction of current flow through the first diode-connected transistor.

14. The semiconductor device according to claim 1, wherein a resistance of the resistance element is one of equal to or greater than 1 gigaohm (GΩ).

15. The semiconductor device according to claim 1, further comprising an array of a plurality of sensors, wherein each sensor of the plurality of sensors includes a respective read electrode, a respective differential amplifier, a respective first capacitor, a respective resistance element, and a respective second capacitor.

16. The semiconductor device according to claim 1, wherein the reference potential is one of a reference potential of the solution or ground.

17. A cell potential measuring device, comprising:

a read electrode configured to read a potential of a cell in a solution;

a differential amplifier including a first input terminal, a second input terminal, and an output terminal, wherein the first input terminal is configured to receive a first input indicating the read potential, the second input terminal is configured to receive a second input, and the output terminal is configured to provide an output of the differential amplifier;

a first capacitor connected with the differential amplifier in series in a loop, wherein the loop feeds back the output of the differential amplifier to the second input terminal of the differential amplifier;

a resistance element connected in parallel with the first capacitor; and a second capacitor connected between a reference electrode and the second input terminal, wherein the reference electrode indicates a reference potential.

\* \* \* \* \*